United States Patent [19]

Naeumann et al.

[11] Patent Number: 4,879,405

[45] Date of Patent: Nov. 7, 1989

[54] PREPARATION OF PENTENOIC ESTERS

[75] Inventors: Fritz Naeumann, Mannheim; Wolfgang Hoelderich; Franz Merger, both of Frankenthal, all of Fed. Rep. of Germany

[73] Assignee: BASF Aktiengesellschaft, Ludwigshafen, Fed. Rep. of Germany

[21] Appl. No.: 205,335

[22] Filed: Jun. 10, 1988

[51] Int. Cl.$^4$ .................... C07C 67/30; C07C 67/343
[52] U.S. Cl. ..................................... 560/211
[58] Field of Search ......................................... 560/211

[56] References Cited

U.S. PATENT DOCUMENTS 3,065,260 11/1962 Konz et al. ........................ 560/211
4,336,403 6/1982 Merger et al. ..................... 560/211

FOREIGN PATENT DOCUMENTS 0081090 5/1987 European Pat. Off. .
1917244 6/1972 Fed. Rep. of Germany .

Primary Examiner—Paul J. Killos
Attorney, Agent, or Firm—Keil & Weinkauf

[57] ABSTRACT

Pentenoic esters are prepared by heating formylvaleric esters at from 50° to 400° C. in the presence of zeolites or one or more phosphates selected from the group consisting of aluminum phosphate, silicon aluminum phosphate, boron aluminum phosphate, silicon iron aluminum phosphate, cerium phosphate, zirconium phosphate, boron phosphate, iron phosphate and strontium phosphate.

11 Claims, No Drawings

PREPARATION OF PENTENOIC ESTERS

If pentenoic esters are hydroformylated by the method described for example in European Pat. Nos. 31,100 and 125,567 the product obtained comprises a mixture of 5-, 4- and 3-formylvaleric esters of varying composition. As for further processing it is desirable to have only one of the isomers at a time, for example the 5-formylvaleric ester, the other isomers are undesirable byproducts.

U.S. Pat. No. 4,517,400 discloses that the dehydrocarbonylation of a mixture of straight-chain and branched aldehydes in the presence of zeolites containing noble metals such as platinum, palladium or rhodium gives olefins. In this process, however, only the straight-chain aldehydes are selectively dehydrocarbonylated, while the branched aldehydes remain intact. For instance, on treatment of a mixture of n- and i-butyraldehyde the n-butyraldehyde is converted into propylene at a rate of from 39 to 56%, while the i-butyraldehyde virtually does not react at all. German Pat. No. 1,917,244 describes a process for dehydrocarbonylating isobutyraldehyde using rhodium-containing alumina as a catalyst. Below 300° C., however, the conversion drops off appreciably, so that the bulk of the isobutyraldehyde used is recovered unchanged. There is no mention of how formylvaleric esters can be converted back into pentenoic esters.

There was in fact no indication for applying the knowledge gained from the case of butyraldehyde to formylvaleric esters since it was known from European Patent No. 81,090 that 4-formylbutyric esters, if heated to 200°-350° C. in the presence of zeolites such as montmorillonite, undergo cyclization to dihydropyrones.

It is an object of the present invention to provide a process for preparing pentenoic esters from formylvaleric esters where the cyclization to dihydropyrones is avoided, which gives high conversions and selectivities and which minimizes the hydrogenation of pentenoic esters to valeric esters.

We have found that this object is achieved with a process for preparing a pentenoic ester by heating a formylvaleric ester at from 50° to 400° C. in the presence of a zeolite or phosphate selected from the group consisting of aluminum phosphate, silicon aluminum phosphate, boron aluminum phosphate, silicon iron aluminum phosphate, cerium phosphate, zirconium phosphate, boron phosphate, iron phosphate and strontium phosphate or mixtures thereof as a catalyst.

The novel process has the advantage of giving high conversions and high selectivities. The novel process further has the advantage of minimizing the hydrogenation of the resulting pentenoic esters to undesirable valeric esters and of avoiding the cyclization to dihydropyrones.

In the light of the cyclization of 4-formylbutyric esters to dihydropyrones which is described in European Patent Application No. 81,090 it had to be expected that branched formylvaleric esters would likewise undergo cyclization to dihydropyrones.

In general, the starting material comprises formylvaleric esters derived from alkanols of from 1 to 12 carbon atoms, cycloalkanols of from 5 to 8 carbon atoms, aralkanols of from 7 to 10 carbon atoms or phenols or naphthols. Preference is given to using alkyl formylvalerates, in particular of alkanols of from 1 to 4 carbon atoms. Suitable compounds are for example the methyl, ethyl, propyl, isopropyl, butyl, hexyl, nonyl, dodecyl, cyclopentyl, cyclohexyl, benzyl and phenyl esters of 5-, 4- and 3-formylvaleric acid. The dehydrocarbonylation of the corresponding 4- and 3-formylvaleric esters has in practice become particularly important. A typical starting mixture contains for example from 50 to 80% by weight of 4-formylvaleric ester, from 20 to 40% by weight of 3-formylvaleric ester and up to 10% by weight of 5-formylvaleric ester.

The reaction is carried out at from 50° to 400° C., advantageously at from 60° to 350° C., in particular at from 70° to 280° C. In general, the reaction is carried out under atmospheric pressure. However, it is also possible to employ slightly reduced or slightly superatmospheric pressure, for example up to 20 bar.

Advantageously, the reaction is carried out in the presence of molecular oxygen or molecular oxygen containing gases which advantageously have a molecular oxygen content of from 5 to 20% by volume. It is possible to use for example air with or without an inert gas, such as nitrogen which, if used, also acts as a carrier gas. It is advantageous to use from 0.05 to 10, in particular from 0.2 to 3, moles of molecular oxygen per mole of formylvaleric ester. The use of molecular oxygen increases the yield of pentenoic ester and prolongs catalyst life.

The use of molecular oxygen was in fact not indicated, since it was known from European Patent Application No. 131,860 that formylvaleric esters are oxidized virtually quantitatively to the corresponding dicarboxylic monoesters even at relatively low temperatures, for example at below 100° C.

It has further proved to be advantageous to carry out the reaction in the presence of diluents which are inert under the reaction conditions. Suitable diluents are for example water, alkanols of from 1 to 6 carbon atoms, such as methanol, ethanol, butanol or hexanol, cycloalkanols of 5 or 6 carbon atoms, such as cyclopentanol or cyclohexanol, ethers such as dioxane or tetrahydrofuran, chlorinated hydrocarbons such as methylene chloride, chloroform or 1,2-dichloroethane, and aliphatic, cycloaliphatic or aromatic hydrocarbons such as benzene, toluene, cyclohexane or paraffins. It is useful to employ from 0.1 to 50, in particular from 0.5 to 20, moles of diluent per mole of formylvaleric ester. Particularly preferred diluents are water and alkanols of from 1 to 6 carbon atoms, and the mixtures thereof.

The process according to the invention is carried out in the presence of zeolites or one or more phosphates selected from the group consisting of aluminum phosphate, silicon aluminum phosphate, boron aluminum phosphate, silicon iron aluminum phosphate, cerium phosphate, zirconium phosphate, boron phosphate, iron phosphate and strontium phosphate.

Advantageously, the said zeolites and phosphates contain one or more metals of group VIII of the periodic table such as palladium, platinum, ruthenium, rhodium, osmium, iridium, iron, cobalt, nickel, in particular noble metals. Particularly preferably, the catalyst contains two metals selected from the group consisting of ruthenium, rhodium, palladium, platinum, iridium and osmium. Good results are also obtained on combining one or more noble metals such as ruthenium, rhodium, palladium, platinum, iridium or osmium with one or more metals of the iron group, for example iron, cobalt or nickel.

Preferably, the level of metal of group VIII of the periodic table is from 0.01 to 10% by weight, preferably from 0.05 to 5% by weight, in particular from 0.05 to 2% by weight, calculated as metal and based on the total of zeolite or phosphate and metal.

It is in addition advantageous for the zeolites and phosphates used to additionally contain one or more elements of groups I–VII of the periodic table, for example zinc, copper, silver, titanium, vanadium, chromium, molybdenum, tungsten, manganese or rhenium. The level of element of groups I–VII of the periodic table is advantageously from 0.05 to 2% by weight, calculated as metal and based on the total zeolite or phosphate and catalytically active metal.

The zeolites used according to the invention have a crystalline, highly ordered structure comprising a three-dimensional network of $Me(IV)O_4$ and $Me(III)O_4$ tetrahedra linked by common oxygen atoms. The electrovalence is balanced by the inclusion of cations, for example alkali metal or hydrogen ions. Suitable trivalent metals (Me(III)) are for example boron, gallium, iron, chromium, vanadium, arsenic, antimony, bismuth, beryllium, in particular aluminum or mixtures thereof, while the tetravalent metals (MeIV) present comprise for example germanium, titanium, zirconium, hafnium, in particular silicon or mixtures thereof.

Advantageous zeolites are aluminosilicate, borosilicate, iron silicate, beryllium silicate, gallium silicate, chromium silicate, arsenic silicate, antimony silicate and bismuth silicate zeolites or mixtures thereof, and also aluminogermanate, borogermanate, gallium germanate and iron germanate zeolites or mixtures thereof.

Good utility is shown by zeolites having a faujasite, erionite or chabasite structure, Y-, X- or L-zeolites, and also zeolites having a pentasil structure. Of these, zeolites having a pentasil structure are particularly preferred. Particularly suitable are aluminosilicate, borosilicate and iron silicate zeolites having a pentasil structure.

Aluminum silicate zeolites are prepared for example from an aluminum compound, preferably aluminum hydroxide or aluminum sulfate, and a silicon component, preferably finely divided silicon dioxide, in an aqueous amine solution, in particular in polyamines such as 1,6-hexanediamine, 1,3-propanediamine or triethylenetetramine, in the presence or in particular in the absence of alkali metal or alkaline earth metal at from 100° to 220° C. under autogenous pressure. This also includes the isotactic zeolites described for example in European Patent Application Nos. 34,727 and 46,504. Aluminosilicate zeolites obtained in this way have an $SiO_2/Al_2O_3$ ratio of from 10 to 40,000, depending on the mixing ratio of the starting materials. Aluminosilicate zeolites having a pentasil structure are also obtainable in an ether medium such as diethylene glycol dimethyl ether, in an alcoholic medium such as methanol or butanol, and also in water. The high-silicon zeolites usable according to invention ($SiO_2/Al_2O_3 \geq 10$) also include the various ZSM types, ferrierite and NU-1. Zeolites of this type are described in U.S. Pat. Nos. 3,702,886, 3,832,449 and 4,076,859; (ferrierite) EP No. 12,473; and (NU-1) U.S. Pat. No. 4,060,590. This group also includes Silicalite ® (U.S. Pat. No. 4,061,724).

Borosilicate zeolites are obtained for example by reacting boric acid with finely divided silica in aqueous amine solution, in particular 1,6-hexanediamine, 1,3-propanediamine or triethylenetetramine in the presence or in particular in the absence of alkali metal or alkaline earth metal at from 90° to 200° C. under autogenous pressure. They also include the isotactic zeolites described in EP Application Nos. 34,727 and 46,494. Suitable reaction media instead of aqueous amine solutions also comprise ethereal solutions, for example diethylene glycol dimethyl ether, or alcoholic solutions, for example 1,6-hexanediol.

Iron silicate zeolites are obtained for example by reacting an iron compound, preferably iron(III) sulfate, with finely divided silica in an aqueous amine solution, in particular 1,6-hexanediamine, in the presence or absence of alkali metal or alkaline earth metal at from 100° to 200° C. under autogenous pressure.

Aluminosilicate, borosilicate and iron silicate zeolites thus prepared, after they have been isolated, dried at from 108° to 160° C., preferably at from 110° to 130° C., and calcined at from 450° to 550° C., preferably at from 480° to 520° C., are in general combined with a binder in a ratio of from 90:10 to 40:60 parts by weight and molded into extrudates or pellets. Suitable binders are aluminum oxides, in particular boehmite, amorphous aluminum silicates having an $SiO_2/Al_2O_3$ ratio of from 25:75 to 90:5, preferably 75:25, and also silica, in particular finely divided silica, and mixtures of finely divided silica and finely divided alumina, titanium dioxide, zirconium dioxide or clay. In general, the extrudates or pellets are dried after molding at from 110° to 130° C. for example for 16 hours and subsequently calcined at from 450° to 550° C., for example for 16 hours.

It is also possible to obtain advantageous catalysts by molding aluminosilicate or borosilicate zeolites immediately after drying and delaying calcination until after the molding. The aluminosilicate and borosilicate zeolites prepared can be used in pure form, without binder, as extrudates or pellets, the extrusion or peptization aids used being for example ethyl cellulose, stearic acid, potato starch, formic acid, oxalic acid, acetic acid, nitric acid, ammonia, amines, silicoesters or graphite or mixtures thereof.

If the zeolites, on account of their manner of preparation, are present for example in the Na-form, they can be completely or partially converted into the H-form by ion exchange, for example with ammonium ions, and subsequent calcination or by treatment with acids. Ion exchange can also be used to incorporate other alkali metal or alkaline earth metal ions, for example lithium, cesium, potassium or magnesium, calcium, strontium or barium.

A further method of modification comprises subjecting zeolites in a molded or unmolded form to a treatment with acids such as hydrochloric acid, hydrofloric acid and phosphoric acid and/or steam.

In a particular embodiment, the acid treatment comprises treating unmolded zeolites at elevated temperatures with hydrofluoric acid, generally from 0.001 to 2N, preferably from 0.05 to 0.5N, hydrofluoric acid, for example by refluxing for example from 0.5 to 5, preferably from 1 to 3, hours. After the zeolites have been separated off, for example by filtration, they are washed and subsequently dried, for example at from 100° to 160° C., and then calcined, for example at from 450° to 600° C.

In another preferred embodiment of the acid treatment, the zeolites, this time after they have been molded together with binders, are treated at elevated temperatures, for example at from 50° to 90° C., in particular at from 60° to 80° C., with preferably from 12 to 20% strength by weight hydrochloric acid for for example from 0.5 to 5 hours. After removal by filtration the zeolites are conveniently washed with water and dried at from 100° to 160° C. and then calcined at from 450° to 600° C. It is also possible first to carry out a treatment with hydrofluoric acid and then a treatment with hydrochloric acid.

If the zeolites are to contain metals of group VIII with or without elements of groups I to VII, these elements are advantageously applied by ion exchange or by impregnating the zeolites.

An ion exchange on the zeolites present in the H-form, ammonium form or alkali metal form can be carried out for example by introducing zeolite extrudates or pellets in a column and circulating an ammoniacal metal salt solution, for example platinum nitrate, through the zeolite packing at elevated temperatures, for example at from 30° to 80° C., for a period of from 15 to 20 hours. This is followed by washing out with water and, as stated above, drying and calcining.

Another method comprises applying metal salts, in particular nitrates which on heating give metal oxides, for example hexachloroplatinate, platinum nitrate, copper nitrate, nickel nitrate or cerium nitrate, to the zeolite in the form of aqueous solutions, by impregnating, and evaporating off any excess water. The impregnated zeolite is then as usual dried and calcined. The impregnating step can be carried out several times in succession until the desired metal content is present. Before use, such metal-containing zeolites are advantageously reduced with hydrogen, for example at from 150° to 300° C. and under atmospheric pressure or a superatmospheric pressure of up to 2 bar.

Of the phosphate catalysts mentioned at the beginning, suitability is shown in particular by those which are obtainable hydrothermally. Of particular importance are aluminum phosphates (APOs) or silicon aluminum phosphates (SAPOs).

Suitable aluminum phosphates (APOs) are for example APO-5, APO-9, APO-11, APO-12, APO-14, APO-21, APO-25, APO-31 and APO-33. Such aluminum phosphates are described for example in S. T. Wilson, B. M. Lok, C. A. Messina, E. A. Flanigen, pages 97–109 in Proc. 6th Fut. Zeolite Conf., Reno 1983, edited by D. M. Olson and A. Bisio.

$AlPO_4$-5 (APO-5) is obtained for example by preparing a homogeneous mixture of orthophosphoric acid with pseudoboehmite in water, adding tetrapropylammonium hydroxide and then heating at from 100° to 200° C. under autogenous pressure for from 20 to 60 hours. The aluminum phosphate thus obtainable is isolated by filtration, dried at for example from 100° to 160° C. and then calcined at from 450° to 550° C.

$AlPO_4$-9 (APO-9) is obtained for example by reacting orthophosphoric acid with pseudoboehmite in an aqueous solution of 1,4-diazobicyclo(2.2.2)octane at from 100° to 200° C. under autogenous pressure for from 200 to 400 hours. If instead of 1,4-diazabicyclo(2.2.2)octane ethylene diamine is used, APO-12 is obtained. Using in the same way an aqueous solution of pyrrolidone at from 150° to 200° C. for from 50 to 200 hours gives APO-21.

Suitable silicon aluminum phosphates (SAPOs) are for example SAPO-5, SAPO-11, SAPO-31 and SAPO-34. Such silicon aluminum phosphates are described for example in E. M. Flanigen, B. M. Lok, R. L. Patton, S. T. Wilson, Pure Appl. Chem., 58 (1986), 1351–1358.

SAPO-5 is obtained for example by mixing a suspension of silicon dioxide in aqueous tetrapropylammonium hydroxide solution with an aqueous suspension of pseudoboehmite and orthophosphoric acid and reacting at from 150° to 200° C. for from 20 to 200 hours under autogenous pressure. After the powder has been filtered off, it is then conveniently dried at from 110° to 160° C. and calcined at from 450° to 550° C.

Suitable silicon aluminum phosphates are also ZYT-5, ZYT-6, ZYT-7, ZYT-9, ZYTL-11 and ZYT-12. Such silicon aluminum phosphates are described for example in Japanese Patent Application 59/217,619.

Suitable aluminum phosphates are also obtained by precipitation. To this end, for example, an aqueous solution of aluminum nitrate is slowly added to an aqueous solution of diammonium hydrogenphosphate while a pH of 6–8 is maintained by the simultaneous addition of, for example, 25% strength ammonia solution. The resulting precipitate is stirred for 12 hours, filtered off with suction and washed and then dried at for example from 100° to 160° C. for from 2 to 24 hours.

Boron phosphates are obtained for example by mixing and kneading concentrated boric acid and phosphoric acid and then drying and calcining in inert gas, air or steam atmosphere at from 250° to 650° C., preferably at from 300° to 500° C.

If the phosphates are to be modified with metals of group VIII and elements of groups I to VII, suitable compounds, such as nitrates which on heating turn into oxides, are applied by impregnating with subsequent drying and calcining.

The catalysts described above are in general used in the form of from 2 to 4 mm extrudates, as pellets from 3 to 5 mm in diameter or as chips from 0.1 to 0.5 mm in size, or in a fluidizable form.

The catalysts used according to the invention show no decrease in activity even over a prolonged period. If, in the use according to the invention, the catalyst undergoes deactivation due to coking, it is advisable to regenerate it by burning off the coke deposit with air or with an air/nitrogen mixture, for example at from 400° to 550° C. On the other hand, it is also possible by a partial precoke to set the activity of the catalyst for optimum selectivity. Specific control over the activity and selectivity is also obtainable by pretreatment with $H_2S$ or sulfur-containing organic compounds at from 150° to 300° C. or by impregnation with an aqueous $(NH_4)_2S$ solution.

The cleavage of formylvaleric ester can be carried out batchwise or, advantageously, continuously as a fixed-bed reaction using fixed catalysts, for example in a liquid phase or trickle bed procedure in the liquid or gas phase. It has also proved useful to carry out the cleavage as a fluidized-bed reaction in the presence of a fluidized catalyst in the gas phase.

In for example a liquid phase embodiment, formylvaleric ester, diluent (if used) and oxygen-containing gas are passed at a temperature below the boiling point of the formylvaleric ester over a fixed catalyst or heated in the presence of a suspended catalyst. The liquid reaction product, after the catalyst has been separated off is then separated by distillation into pentenoic ester and unconverted formylvaleric ester which may be recycled.

In for example a preferred embodiment of the process according to the invention in the gas phase, a mixture of formylvaleric ester and diluent is vaporized and then passed together with air and conveniently a carrier gas such as nitrogen, carbon dioxide or argon into a fixed or fluidized catalyst bed at the aforementioned temperature. The output from the reaction is condensed and then separated by fractional distillation. Unconverted formylvaleric ester is conveniently recycled.

Using the process according to the invention it is possible to cleave unwanted isomers of formylvaleric esters back into a mixture of 4-, 3- and 2-pentenoic esters and to resubject the latter to hydroformylation. As a result it is possible to convert pentenoic esters virtually completely into the desired isomer of 5-formylvaleric ester.

5-Formylvaleric ester is suitable for example for preparing aminocaproic ester which is converted into caprolactam.

The process of the invention is illustrated by the following Examples:

EXAMPLES 1 TO 16

The reaction is carried out in the gas phase under isothermic conditions in a tubular reactor (helix, 0.6 cm in internal diameter, 90 cm in length) for not less than 6 hours. The gaseous reaction outputs are condensed in cold traps and weighed, and the reaction products are separated and characterized in a conventional manner. The quantitative determination of the reaction products and the starting materials is done by gas chromatography. The details are given below.

The Examples are carried out using the following catalysts. The following abbreviations are used: PAE - pentenoic ester, FVAE - formylvaleric ester, VAE - valeric ester.

Catalyst A

A borosilicate zeolite of the pentasil type is prepared in a hydrothermal synthesis from 640 g of finely divided $SiO_2$, 122 g of $H_3BO_3$, 8000 g of an aqueous 1,6-hexanediamine solution (mixture 50:50% by weight) at 170° C. under autogenous pressure in a stirred autoclave. After filtration and washing the crystalline reaction product is dried at 100° C./24 h and calcined at 500° C./24 h. This borosilicate zeolite comprises 94.2% by weight of $SiO_2$ and 2.3% by weight of $B_2O_3$. This material is molded with a molding aid into 2 mm extrudates which are dried at 110° C./16 h and calcined at 500° C./24 h.

Catalyst B

Catalyst B is obtained by ion exchange on the unextruded powder of catalyst A with an aqueous $Pd(NO_3)_2$ solution. After drying at 110° C./2 h and calcination at 500° C./2 h the material is molded with a molding aid into 2 mm extrudates which are dried at 110° C./16 h and calcined at 500° C./24 h. The palladium content is 1.1% by weight (based on the total weight).

Catalyst C

The borosilicate zeolite extrudates of catalyst A are impregnated with an ammoniacal palladium nitrate solution. Washing out with water is followed by drying at 110° C. and calcination at 500° C./5 h. The Pd content is 1.2% by weight.

Catalyst D

Catalyst D is prepared in the same way as catalyst B, except that the ion exchange is performed with an aqueous solution of $H_2[PtCl_6]$ instead of Pd nitrate. The Pt content is 1.9% by weight.

Catalyst E

Catalyst E is prepared in the same way as catalyst C, except that the impregnating is effected with an aqueous solution of $RhCl_3$ instead of Pd nitrate. The Rh content is 1.0% by weight.

Catalyst F

Catalyst F is prepared in the same way as catalyst C, except that the impregnating is effected with an aqueous solution of Pd nitrate and Na nitrate. The Pd content is 1.0% by weight and the Na content 0.25% by weight.

Catalyst G

Catalyst G is prepared in the same way as catalyst B, except that the ion exchange is carried out with an aqueous solution of Pd nitrate and Zn nitrate. The Pd content is 1.1% by weight and the Zn content 1.0% by weight.

Catalyst H

Catalyst H is prepared in the same way as catalyst B, except that the ion exchange is carried out with an aqueous solution of Pd nitrate and Ni nitrate. Both the Pd and the Ni content are 1.1% by weight.

Catalyst I

Catalyst I is prepared in the same way as catalyst B, except that the ion exchange is carried out with an aqueous solution of $RhCl_3$ and Co nitrate. Both the Rh and Co content are 1.0% by weight.

Catalyst K

Catalyst K is prepared in the same way as catalyst B, except that the ion exchange is carried out with an aqueous solution of $RhCl_3$ and $RuCl_3$. The Rh content is 1.0% by weight and the Ru content 0.7% by weight.

Catalyst L

Catalyst L is prepared in the same way as catalyst B, except that the ion exchange is carried out with an aqueous solution of $RhCl_3$, $H_2[PtCl_6]$ and $RuCl_3$. The Rh, Pt and Ru contents are all 1.0% by weight.

Catalyst M

Silicon aluminum phosphate 5 (SAPO-5) is prepared from a mixture of 200 g of 98% strength phosphoric acid, 136 g of boehmite, 60 g of silica sol (30% strength), 287 g of tripropylamine and 587 g of $H_2O$. This mixture is reacted at 150° C. under autogenous pressure for 168 hours. After filtration the crystalline product is dried at 120° C. and calcined at 500° C. SAPO-5 contains 49.8% by weight of $P_2O_5$, 33.0% by weight of $Al_2O_3$ and 6.2% by weight of $SiO_2$. SAPO-5 is molded with an extrusion aid into 3 mm extrudates, which are dried at 120° C. and calcined at 500° C.

The extrudates are then impregnated with an ammoniacal palladium nitrate solution. Washing with $H_2O$ was followed by drying at 110° C. and calcination at 500° C./5 h. The Pd content is about 1% by weight.

Catalyst N

Catalyst N comprises a Pd doped aluminum phosphate obtained by precipitation from $Al(NO_3)_3/H_3PO_4$ solution with aqueous $NH_3$ solution at pH 6–7. The precipitate is filtered off and dried at 110° C. and calcined at 500° C. The Al content is 28.5% and the P content 13.2%. The aluminum phosphate is molded with an extrusion aid into 3 mm extrudates which are dyed at 120° C. and calcined at 500° C.

The extrudates are then impregnated with ammoniacal palladium nitrate solution. Washing with H₂O is followed by drying at 110° C. and calcination at 500° C./5 h. The Pd content is about 1% by weight.

Table I gives for each of Examples 1 to 11 the FVAE, PAE and VAE contents of the reaction outputs after 6 hours (FVAE=methyl formylvalerate, PAE=methyl pentenoate, VAE=methyl valerate).

EXAMPLE 1

Per hour about 10 ml of a mixture of methyl 4-formylvalerate (4-FVAE), tetrahydrofuran and water (23% by weight of 4-FVAE, 10% by weight of water, the rest tetrahydrofuran) were passed together with 3 l of nitrogen at 200° C. over 7 g of catalyst G (Table 1).

EXAMPLE 2

Per hour, about 10 ml of a mixture of 4-FVAE, methanol and water (23% by weight of 4-FVAE, 10% by weight of water, the rest tetrahydrofuran) were passed together with 3 l of nitrogen at 200° C. over 7 g of catalyst G (Table 1).

EXAMPLE 3

Per hour, about 10 ml of a mixture of methyl 4-formylvalerate (4-FVAE), tetrahydrofuran and water (23% by weight of 4-FVAE, 10% by weight of water, the rest tetrahydrofuran) were passed together with 1 l of air and 2 l of nitrogen at 200° C. over 7 g of catalyst G (Table 1).

EXAMPLE 4

Per hour, about 10 ml of a mixture of 4-FVAE, methanol and water (23% by weight of 4-FVAE, 10% by weight of water, the rest methanol) were passed together with 1 l of air and 2 l of nitrogen at 200° C. over 7 g of catalyst G (Table 1).

EXAMPLES 5 TO 7

Per hour about 10 ml of a mixture of 4-FVAE, methanol and water (23% by weight of 4-FVAE, 10% by weight of water, the rest methanol) were passed together with 1 l of air and 2 l of nitrogen at 200° C. over 7 g of catalyst B or E or I (Table 1).

EXAMPLES 8 AND 9

Per hour, about 10 ml of a mixture of 4-FVAE, 3-FVAE, methanol and water (14.5% by weight of 4-FVAE, 7.4% by weight of 3-FVAE, 10% by weight of water, the rest methanol) were passed together with 3 l of air at 185° C. over 7 g of catalyst C or F (Table 1).

EXAMPLES 10 AND 11

Per hour, about 10 ml of a mixture of 4-FVAE, methanol and water (23% by weight of 4-FVAE, 10% by weight of water, the rest methanol) were passed together with 1 l of air and 2 l of nitrogen at 200° C. over 7 g of catalyst K or L (Table 1).

TABLE 1

| Example | 1 | 2 | 3 | 4 | 5 | 6 | 7 | 8 | 9 | 10 | 11 |
|---|---|---|---|---|---|---|---|---|---|---|---|
| Catalyst | G | G | G | G | B | E | I | C | F | K | L |
| Temperature | 200° C. | 200° C. | 200° C. | 200° C. | 200° C. | 200° C. | 200° C. | 185° C. | 185° C. | 200° C. | 200° C. |
| WHSV h⁻¹ | 1.2 | 1.2 | 1.2 | 1.2 | 1.1 | 1.1 | 1.2 | 1.0 | 1.2 | 1.2 | 1.2 |
| FVAE area % | 65 | 33 | 79 | 2 | — | — | 4 | — | — | 20 | — |
| PAE area % | 21 | 21 | 14 | 65 | 79 | 55 | 62 | 79 | 69 | 47 | 56 |
| VAE area % | 5 | 12 | 2 | 24 | 13 | 31 | 21 | 4 | 2 | 11 | 32 |

EXAMPLE 12

In a long-term run over 122 hours, every hour about 10 ml of a mixture of 4-FVAE, methanol and water (23% by weight of 4-FVAE, 10% by weight of water, the rest methanol) were passed together with 1 l of air and 1 l of nitrogen at 200° C. over 7 g of catalyst G. Table 2 gives the FVAE, PAE and VAE contents of the reaction outputs after so many hours of the run.

TABLE 2

| No. | Run time (h) | PAE (area %) | VAE (area %) | FVAE (area %) |
|---|---|---|---|---|
| 1 | 6 | 71 | 16 | 2 |
| 2 | 22 | 73 | 19 | 1 |
| 3 | 46 | 72 | 18 | 1 |
| 4 | 78 | 67 | 24 | 2 |
| 5 | 102 | 69 | 21 | 2 |
| 6 | 122 | 71 | 22 | 1 |

After the run of 122 hours the combined reaction outputs were analyzed quantitatively:

Output: 695 g of methyl pentenoate/methyl valerate/solvent mixture (12% by weight of pentenoic ester (8% of methyl 4-, 50% of methyl 3- and 42% of methyl 2-trans-pentenoate)/5% of valeric ester +2-cis-PAE)

EXAMPLE 13

In a long-term run over 30 hours, every hour 11 g of a 4-FVAE- and 3-FVAE-containing mixture (63% by weight of 4-FVAE, 32% by weight of 3-FVAE) were pumped into a vaporizer and passed from there together with 3 l of air and 7 l of nitrogen at 200° C. over 7 g of catalyst F. The gaseous reaction outputs after 30 hours were weighed and analyzed by gas chromatography (total starting quantity: 336 g of FVAE). Table 3 gives the FVAE, PAE and VAE contents of the reaction outputs after so many hours of the run.

TABLE 3

| No. | Run time (h) | PAE (area %) | VAE (area %) | FVAE (area %) |
|---|---|---|---|---|
| 1 | 6 | 59 | 18 | 19 |
| 2 | 11 | 61 | 18 | 17 |
| 3 | 19 | 60 | 16 | 20 |
| 4 | 27 | 54 | 12 | 30 |

After the run of 30 hours the combined reaction outputs were analyzed quantitatively:

Output: 312 g of methyl pentenoate/methyl valerate/solvent mixture (46% by weight of pentenoic ester (13% of methyl 4-, 65% of methyl 3- and 22% of methyl 2-trans-pentenoate)/16% by weight of valeric ester +2-cis-PAE) 63% conversion, 85% selectivity to pentenoic ester

EXAMPLE 14

For 6 hours, every hour 12 g of a 4-FVAE- and 3-FVAE-containing mixture (63% of 4-FVAE, 32% of 3-FVAE) were pumped into a vaporizer and passed from there together with 8 l of air and 3 l of nitrogen at 185° C. over 7 g of catalyst C. The condensed reaction outputs obtained after the run of 6 hours were weighed and analyzed by gas chromatography (Table 4).

EXAMPLE 15

For a period of 6 hours, every hour 11 g of a 4-FVAE- and 3-FVAE-containing mixture (63% of 4-FVAE, 32% of 3-FVAE) were pumped into a vaporizer and passed from there together with 6 l of air and 5 l of nitrogen at 185° C. over 7 g of catalyst M. The condensed reaction outputs after the run of 6 hours were weighed and analyzed by gas chromatography (Table 4).

EXAMPLE 16

For a period of 6 hours, every hour 11 g of 5-FVAE were pumped into a vaporizer and passed from there together with 11 l of nitrogen at 185° C. over 7 g of catalyst F.

The condensed reaction outputs after the run of 6 hours were weighed and analyzed by gas chromatography (Table 4).

TABLE 4

| Example | Catalyst | Starting mixture | PAE (wt. %) | VAE (wt. %) | FVAE (wt. %) | Conversion % | Selectivity to PAE % |
|---|---|---|---|---|---|---|---|
| 14 | C | ¾-FVAE | 70 | 10 | 13 | 88 | 88 |
| 15 | M | ¾-FVAE | 25 | 5 | 50 | 45 | 65 |
| 16 | F | 5-FVAE | 30 | 16 | 45 | 65 | 45 |

We claim:

1. A process for preparing a pentenoic ester, which comprises: heating a formylvaleric ester at from 50° to 400° C. in the presence of a zeolite or one or more phosphates selected from the group consisting of aluminum phosphate, silicon aluminum phosphate, boron aluminum phosphate, silicon iron aluminum phosphate, cerium phosphate, zirconium phosphate, boron phosphate, iron phosphate and strontium phosphate.

2. The process of claim 1, wherein molecular oxygen or a gas containing molecular oxygen is present.

3. The process of claim 1, wherein a diluent which is inert under the reaction conditions is present.

4. The process of claim 1, wherein the zeolite or phosphate contains one or more metals of group VIII of the periodic table.

5. The process of claim 4, wherein the zeolite or phosphate contains one or more noble metals.

6. The process of claim 5, wherein the zeolite or phosphate additionally contains one or more metals of the iron group.

7. The process of claim 1, wherein the zeolite or phosphate additionally contains one or more elements of groups I–VII of the periodic table.

8. The process of claim 1, wherein a zeolite having a pentasil structure is used.

9. The process of claim 1, wherein aluminum silicate zeolite, boron silicate zeolite or iron silicate zeolite having a pentasil structure is used.

10. The process of claim 1, wherein aluminum silicate zeolite having a faujasite structure is used.

11. The process of claim 1, wherein aluminum phosphate, silicon aluminum phosphate, iron aluminum phosphate or boron aluminum phosphate is used.

* * * * *

UNITED STATES PATENT AND TRADEMARK OFFICE
CERTIFICATE OF CORRECTION

PATENT NO. : 4,879,405
DATED : November 7, 1989
INVENTOR(S) : Fritz NAEUMANN et al.

It is certified that error appears in the above-identified patent and that said Letters Patent is hereby corrected as shown below:

ON TITLE PAGE:

insert --Foreign Application Priority Data

June 15, 1987   Federal Republic of Germany ... 3719935--

Column 12, line 18

Claim 7, Line 1

"claim 1" should read --claim 4--

Signed and Sealed this

Third Day of December, 1991

Attest:

HARRY F. MANBECK, JR.

Attesting Officer      Commissioner of Patents and Trademarks